United States Patent [19]

Behring et al.

[11] Patent Number: 5,601,185

[45] Date of Patent: Feb. 11, 1997

[54] PACKAGE WITH SURGICAL SUTURE MATERIAL

[75] Inventors: Rainer Behring, Itzstedt; Ulrich Schnoor, Bad Bramstedt, both of Germany

[73] Assignee: Ethicon, Inc., Somerville, N.J.

[21] Appl. No.: 512,729

[22] Filed: Aug. 8, 1995

[51] Int. Cl.⁶ ................................................ A61B 17/06
[52] U.S. Cl. ........................................ 206/63.3; 206/380
[58] Field of Search .............................. 206/63.3, 380, 206/382, 383, 477, 478, 480, 227

[56] References Cited

U.S. PATENT DOCUMENTS

| | | | |
|---|---|---|---|
| 2,692,676 | 10/1954 | Grover | 206/63.3 |
| 3,985,227 | 10/1976 | Thyen et al. | 206/63.3 |
| 4,120,395 | 10/1978 | Mandel et al. | 206/63.3 |
| 4,135,623 | 1/1979 | Thyen | 206/63.3 |
| 4,391,365 | 7/1983 | Batchelor | 206/63.3 |
| 4,615,435 | 10/1986 | Alpern et al. | 206/63.3 |
| 4,896,767 | 1/1990 | Pinheiro | 206/63.3 |
| 4,946,043 | 8/1990 | Roshdy et al. | 206/63.3 |
| 5,024,322 | 6/1991 | Holzwarth | 206/63.3 |
| 5,199,561 | 4/1993 | Roshdy et al. | 206/63.3 |
| 5,236,082 | 8/1993 | Brown | 206/63.3 |
| 5,279,411 | 1/1994 | Brunken | 206/63.3 |
| 5,301,801 | 4/1994 | Sinn | 206/63.3 |
| 5,344,005 | 9/1994 | Kettner et al. | 206/68.3 |
| 5,358,102 | 10/1994 | Brown | 206/63.3 |
| 5,386,912 | 2/1995 | Holzwarth et al. | 206/63.3 |
| 5,427,243 | 6/1995 | Roshdy | 206/438 |

*Primary Examiner*—Jacob K. Ackun
*Attorney, Agent, or Firm*—Emil Richard Skula

[57] ABSTRACT

A package with surgical suture material contains a needle-holding section (6) and two thread-holding sections (7) connected thereto. Closure plates (35, 36) are attached to the long edges of the needle-holding section (6). Arranged at the lower short edge (5) of the lower thread-holding section (7) is a cover plate (37) which likewise has closure plates (38, 39) at its long edges. A thread holder (15) and a needle holder (16) are provided on the needle-holding section (6). Arranged on the thread-holding sections (7) are in each case two thread holders (15). Several needle-thread combinations (20, 21) or individual threads (21) are held by this needle holder (16) and the thread holders (15). The individual sections (6, 7) are folded in such a way that in each case they lie against one another. The closure plates (35, 36) serve to safeguard the folded arrangement of the sections (6, 7) against unfolding. The needles (20) secured on the needle-holding section (6) are covered by the cover plate (37), the closure plates (38, 39) holding the cover plate (37) in this position.

1 Claim, 6 Drawing Sheets

PACKAGE WITH SURGICAL SUTURE MATERIAL

FIELD OF THE INVENTION

The invention relates to a package with surgical Suture material, in particular as an inner package in sterile packages.

BACKGROUND OF THE INVENTION

Surgical suture material is used in the form of threads reinforced with needles, i.e. needle-thread combinations, and optionally also in the form of individual threads in pre-cut lengths. Various types of material are available for the threads, such as for example silk, polyamides, polypropylene or woven polyesters and resorbable materials, in various thread thicknesses and thread lengths. The threads can be connected with a number of different straight and bent needles which differ in needle size, needle thickness and type of section.

The package of surgical suture material has to guarantee that the contents remain safe and sterile. Usually, a sterile inner package is enclosed by an outer cover which keeps the inner package sterile until it is torn open and removed during an operation. The inner package, which is described in the following as "package", should allow the surgical suture material to be removed rapidly and without complication. In particular, the thread to be removed should not become entangled or entwined, and moreover, it is to be ensured that the thread, after its removal, does not have a tendency to return to the shape in which it was positioned in the package ("thread memory").

U.S. Pat. No. 3,985,227 shows a package for needle-thread combinations which satisfies these requirements by having several needle-thread combinations arranged spaced apart in parallel and storing them lengthwise in a folding package, without them being kinked in the process. Kinks or other deformations in the thread, which promote the thread memory effect, are avoided in this way. Nor can the thread thus become entangled. For removal, the thread is pulled out from the upper end of the folding package.

It is a disadvantage with this previously known package that, because of the type of storage, the longitudinal dimension of the package must be greater than the length of the needle-thread combinations stored therein, as a result of which the package becomes very unwieldy or the length of the thread is limited.

SUMMARY OF THE INVENTION

It is the object of the invention to provide a package with surgical suture material which has a compact and manageable shape even in the case of longer threads and also permits simple and reliable removal of the needle-thread combinations and of the individual threads contained therein.

This object is achieved by a package with surgical suture material having the features of patent claim 1. Advantageous embodiments arise from the dependent claims.

The package with surgical suture material has an elongated base plate with a first long edge, a second long edge, an upper short edge and a lower short edge. Arranged transversely to the long edges are folds, by means of which the base plate is divided into a needle-holding section starting at the upper short edge and one or more thread-holding sections connected thereto. Attached to the needle-holding section is a needle holder and on each of the thread-holding sections at least One thread holder which runs transversely to the long edges. If desired, an additional thread holder can be arranged on the needle-holding section in the proximity of the needle holder.

The threads of the needle-thread combinations are disposed onto the base plate, whereby the threads lie on the thread-holding sections and the front ends of the threads, with the needles attached thereto, lie on the needle-holding section. The threads are held by the thread holders and the-needles are held by the needle holder in such a way that the needle-thread combinations are spaced apart from one another and are preferably arranged in essentially parallel manner to the long edges of the base plate. The package is naturally also suitable for threads without needles. Here, in an otherwise identical arrangement of the threads, the front end of the thread, instead of the needle, is held by the needle holder.

The thread holders and the needle holder are preferably attached only to the front face of the base plate. Alternatively, the sections of the base plate can however also be designed so that the thread holders are located on the front faces of the sections and the needle holder and optionally other thread holders are attached to the rear face of individual sections. The threads are held by the thread holders attached to the front face of the base plate, the front thread ends are bent around a short edge of the base plate and the front thread ends, with the needles optionally attached thereto, are attached to the thread holders and the needle holder arranged on the rear face of the base plate. Further, the rear ends of the threads can be bent around the other short edge of the base plate and can be secured to the thread holders arranged on the rear face of the base plate.

As described above, folds at which the base plate can be folded are provided transversely to the long edges of the base plate. Such a folding or kinking line is preferably created by a double fold, by means of which it is ensured that the regions to be folded, i.e. the thread-holding sections and the needle-holding section, are kept spaced apart from one another in the folded state. At kinking lines where the threads are guided around the kinking edge, the folds can also be formed as a series of holes, as a result of which a fluted edge is formed upon folding, which serves as an additional guiding means for the threads.

At the described kinking lines, the needle-holding section and the thread-holding sections provided with the needle-thread combinations are folded in the form of a concertina, with the result that there are different folding options depending on the number of kinking lines. With one kinking line, the base plate is preferably folded in a V-shape, with two kinking lines-in a N-shape and with three kinking lines, in a W-shape. The length of the package is correspondingly reduced by this folding procedure.

As a result of the concertina-shaped folding technique, the front faces and the rear faces of the individual needle-holding section and the thread-holding sections in each case lie opposite one another. As described above, the needle holder and the thread holders are preferably arranged on the front face of the base plate. Since the needle holder and the thread holders form a certain spatial elevation, the front faces of the base plate are held in spaced-apart manner by the holders, whilst the rear faces, as long as no holders are attached to them, lie directly against one another. This also explains the advantageous use of the double folds, by means of which a double kinking line is formed, the result of which is that the sections spaced by the holders are arranged essentially parallel to one another.

The individual threads are preferably attached to the front face of the base plate and follow the fold pattern of the base plate. In the areas where the front faces of the sections of the folded base plate lie opposite one another in spaced-apart manner, the threads consequently also lie directly opposite one another. In the areas where the rear faces of the folded base plate lie directly opposite one another, the threads secured to the associated front faces of the sections are separated by precisely these sections.

With all folding options, the needle-holding section is always arranged such that the needle holder with the needles or thread ends held by it is located on a surface of the package directed towards the outside. In this way the needle with the thread attached to it or the individual thread end can be gripped from the outside and removed from the folded package.

In order to keep the folded base plate with the needle-thread combinations or individual threads held by the needle holder and the thread holders in its folded state, closure devices are provided at the base plate. These closure devices are preferably arranged at the long edges of the base plate, at the upper end of the long edge in the region of the needle-holding section.

The closure devices are preferably closure plates which are constructed as one piece with the base plate via double folds. These closure plates are bent around the folded package and brought into engagement with one another via closure means.

In order to protect the needles and the front thread ends held at the outer surface of the package from contact, a cover plate is provided on the base plate or constructed as one piece with the base plate via a double fold. The cover plate is preferably arranged on the lower short edge of the base plate and can be folded over towards the package in such a way that it covers the part of the surface of the package on which the needles and the front thread ends are held. In order to keep the cover plate in its folded-over state, closure devices are likewise provided on the cover plate. The closure devices are preferably closure plates which are constructed as one piece with the cover plate via double folds. These closure plates are folded around the folded package and brought into engagement with one another via closure means. In order to open the cover-plate to remove the needle-thread combinations or the individual threads, the closure devices are released and the cover plate is folded away from the package, as a result of which the needles and the front thread ends lie uncovered and can be removed.

Because the individual needles and threads are arranged spaced apart alongside one another by the needle holder and the thread holders on the base plate and held such that they do not mutually impede one another, even when the base plate is folded, it is ensured that the thread cannot become entwined upon removal from the package. When the surgeon grips the needle or the front thread end with a gripping-device, he first pulls the needle or the front thread end from the needle holder, then the individual thread sections are pulled one after the other through the thread holders and removed from them.

With this arrangement of the folded sections of the base plate and the thread holders, thread sections which lie opposite one another are prevented from slipping and running into one another, which would lead to problems when removing the thread. It has been shown that due to the spaced-apart arrangement of the individual sections of the base plate, narrow bending radii or even kinks of the threads are prevented so that the thread memory effect is reliably avoided.

The thread holders are preferably formed as strips which are provided with holding slots and glued onto the base plate. These strips preferably consist of foam, for example a silicone foam. The strip can be constructed in such a way that its cross-section varies. For example, one side edge of the strip can be constructed in zigzag manner, as a result of which the cross-sectional area of the strip changes and different side areas of the holding slot are obtained. It is advantageous to place thicker threads in slots with a large side area and thinner threads in slots with a small side Area. The strip can have different cross-sectional shapes, but preferably has a triangular cross-section, whereby the glue surface runs flat and the adjacent surfaces can be constructed in flat or curved manner. In a preferred embodiment, one of the interior angles, laid at the adhesive surface, of the triangle is larger than 90°, as a result of which an undercut is formed.

The thread holders-are preferably arranged so that the face of the strip on which this undercut is located is placed in the direction in which the thread moves when it is pulled out from the package. If the thread held in the slot of the thread holder is, on removal, now pulled in the direction of pull, it moves, because of the described cross-sectional shape, out from the slot and can be removed from the package with reduced application of force, without high forces of friction or even a blocking being able to arise.

The needle holder can also be secured in ways other than by gluing. The holding slots are preferably cut into the needle holder in accordance with the shape of needle. This simplifies removal of the needle and the gripping position is always the same.

The package is designed as a folding package and can therefore be produced inexpensively. It consists—optionally except for the needle holder and the thread holders—of a uniform material, preferably cardboard.

The invention is described in more detail below with reference to an embodiment. The diagrams show:

FIG. 1 a top view of a blank for an embodiment of the package, the front face of the base plate being directed upwards, FIGS. 2 to 4 perspective views of the package from FIG. 1, whereby it is shown how the individual sections of the package are folded together, FIG. 5 a longitudinal cross-section of the folded package from FIG. 1, FIG. 6a a top view of a thread holder, and FIG. 6b a cross-section of the thread holder along line b—b from FIG. 6a.

DESCRIPTION OF THE PREFERRED EMBODIMENTS

Figure 1:
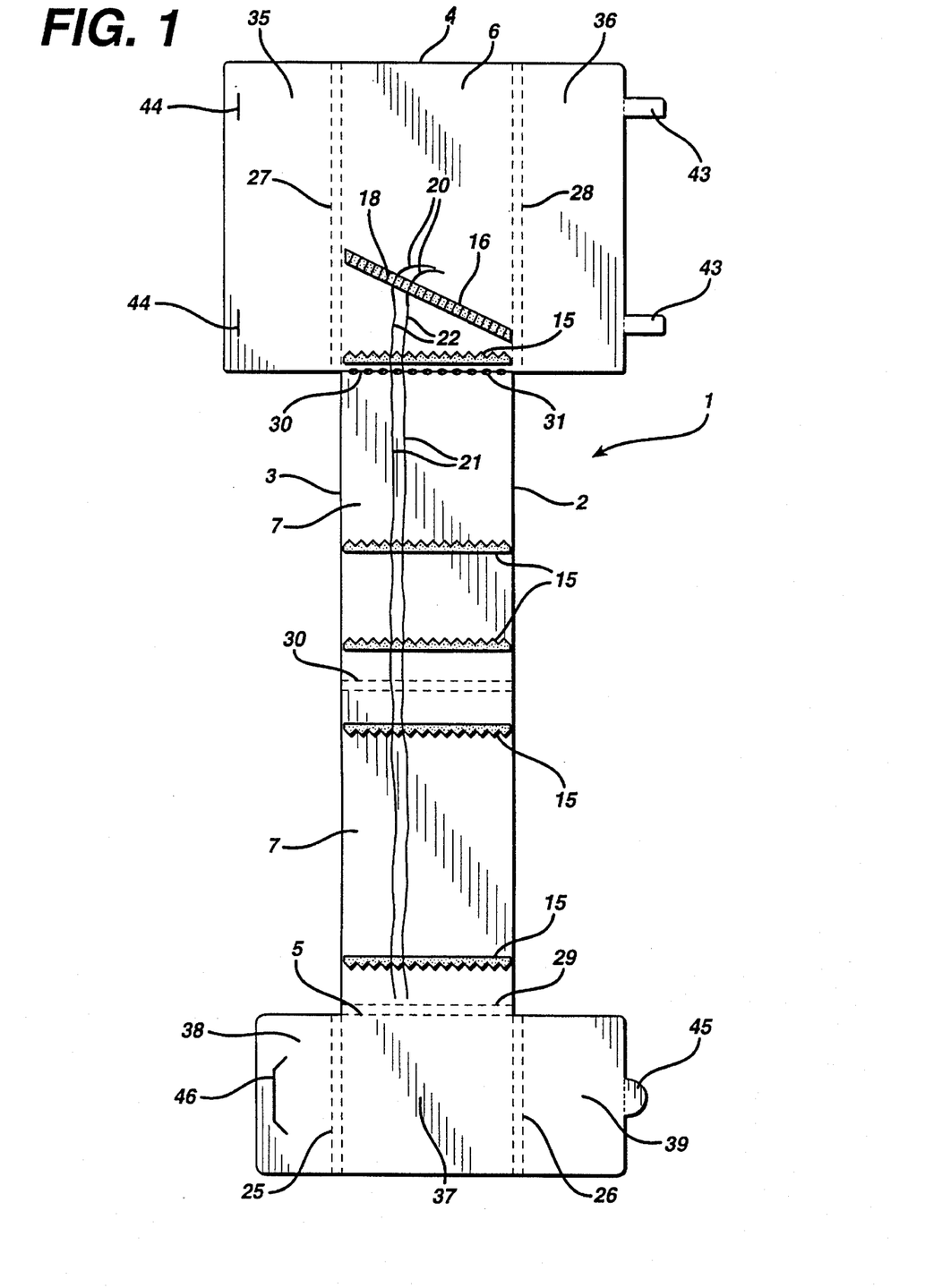

FIG. 1 shows the blank for an embodiment of the package. The blank preferably consists of cardboard. Fold lines are represented by the dashed lines.

A base plate 1 has an essentially rectangular base shape with a first long edge 2, a second long edge 3, an upper short edge 4 and a lower short edge 5.

Folds 30, or a series of holes 31, are provided transversely to the long edges 2, 3, as a result of which the base plate 1 is divided into several sections. Arranged in the upper region of the base plate 1, starting at the upper short edge 4, is a needle-holding section 6. Connected to this, divided in bendable manner by a fold 30 or a series of holes 31, two thread-holding sections 7 are arranged, which are again divided by a double fold 30 in bendable manner. Arranged at the lower short edge 5 is a cover plate 37 which is connected via a double fold 29 to the lower thread-holding section 7.

Arranged at the long edges of the needle-holding section 6 via double folds 27, 28 are two closure plates 35, 36. The closure plates 35, 36 in turn have at their long edges closure means in the form of tabs 43 and incisions 44. Provided at the long edges of the cover plate 37, likewise via double folds 25, 26, are closure plates 38, 39 which have one tab 45 and one incision 46.

A needle holder 16 running at an angle and a thread holder 15 running parallel to the series of holes 31 are arranged on the needle-holding section 6, on the front face of the base plate 1 which is directed upwards in FIG. 1. On each of the thread-holding sections 7 are arranged two thread holders 15 which run transversely to the long edges 2, 3.

Figure 6A:
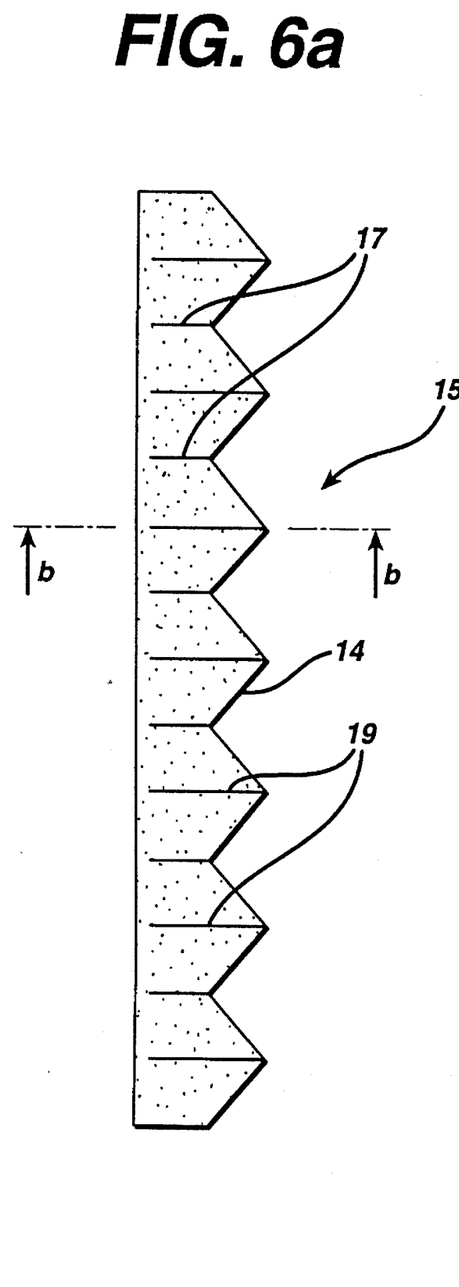
Figure 6B:
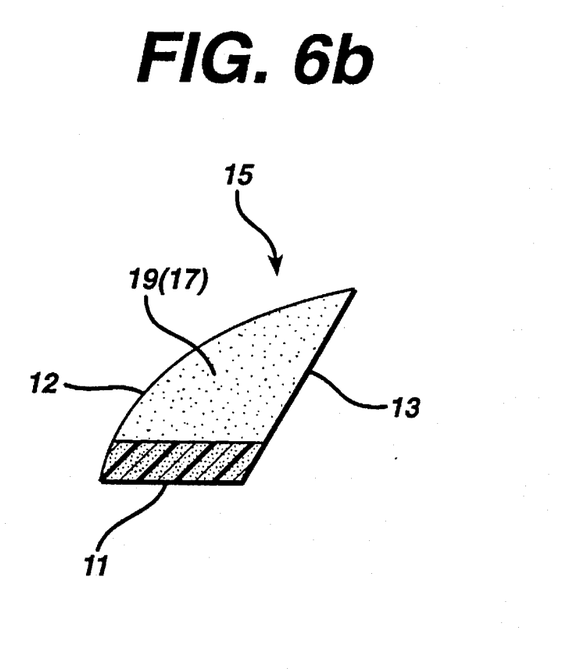

The threads 21 of needle-thread combinations 20, 21 are disposed onto the base plate 1, whereby the threads 21 are held by holding slots 17, 19 which are provided in the thread holders 15 (see also FIG. 6). The needles 20 are held by holding slots 18 which are provided in the needle holder 16. The holding slots 17, 18, 19 are arranged essentially at the same distance so that the needle-thread combinations 20, 21 secured in the holding slots are arranged spaced apart from one another in essentially parallel manner.

Figure 2:
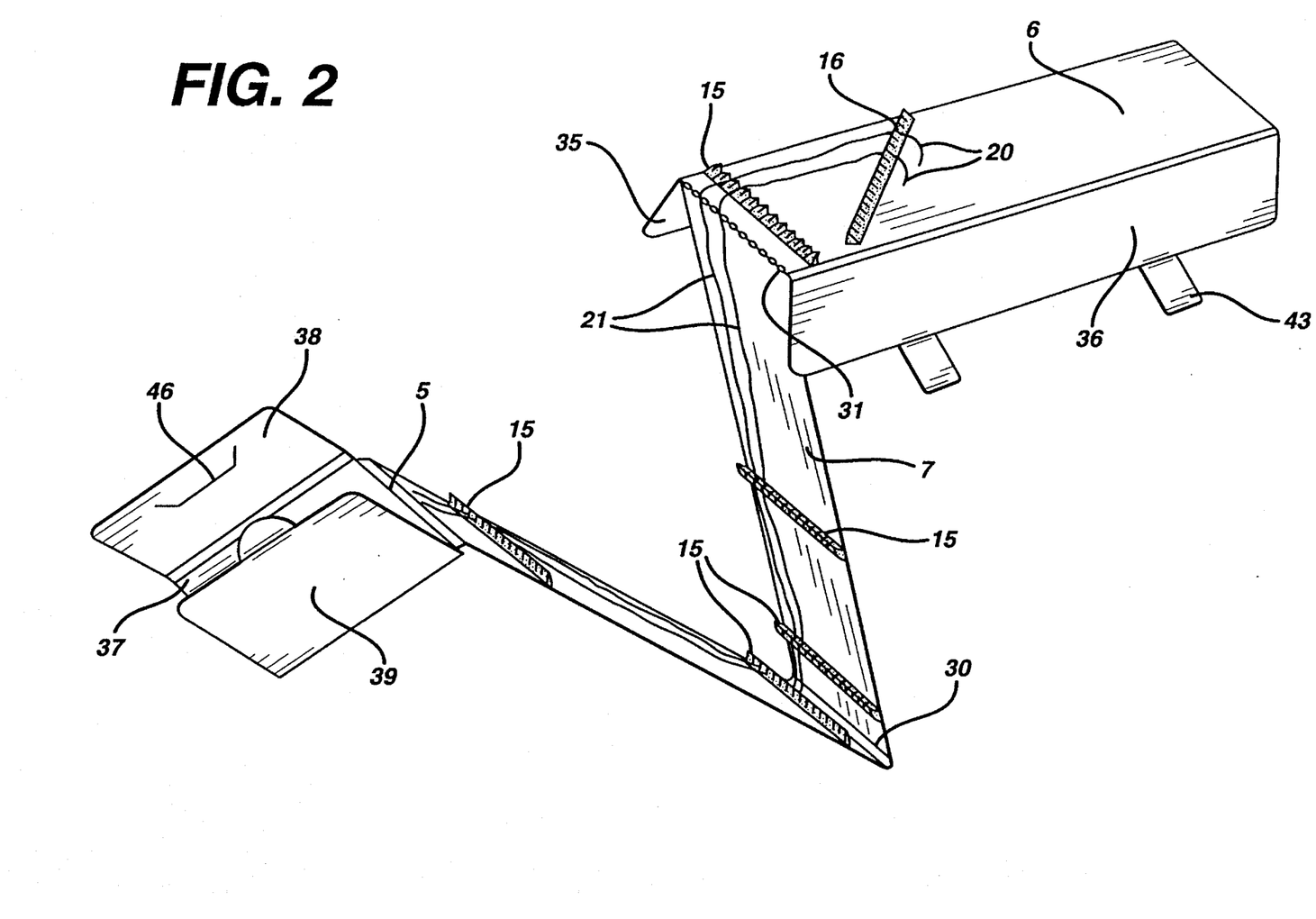
Figure 3:
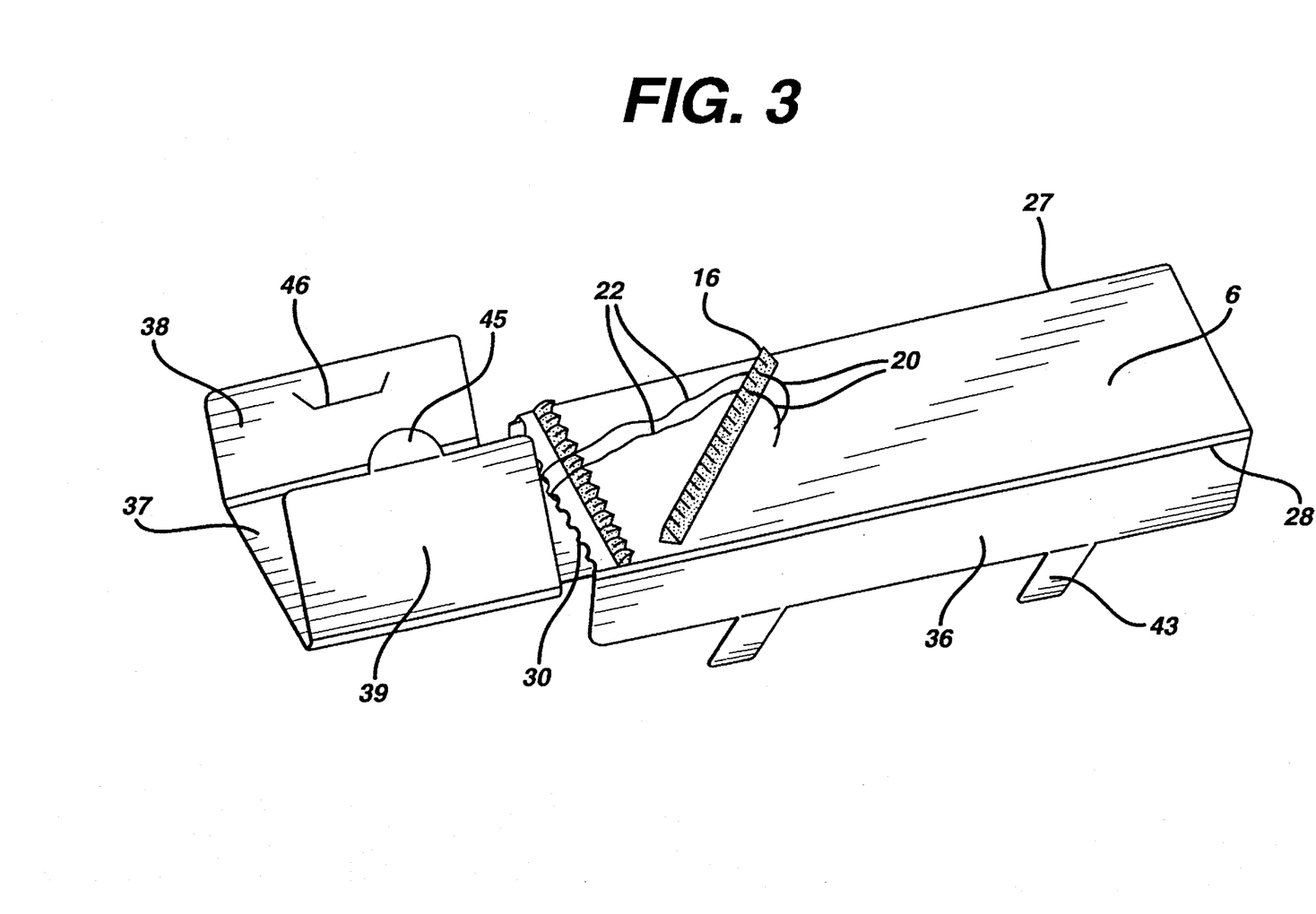
Figure 4:
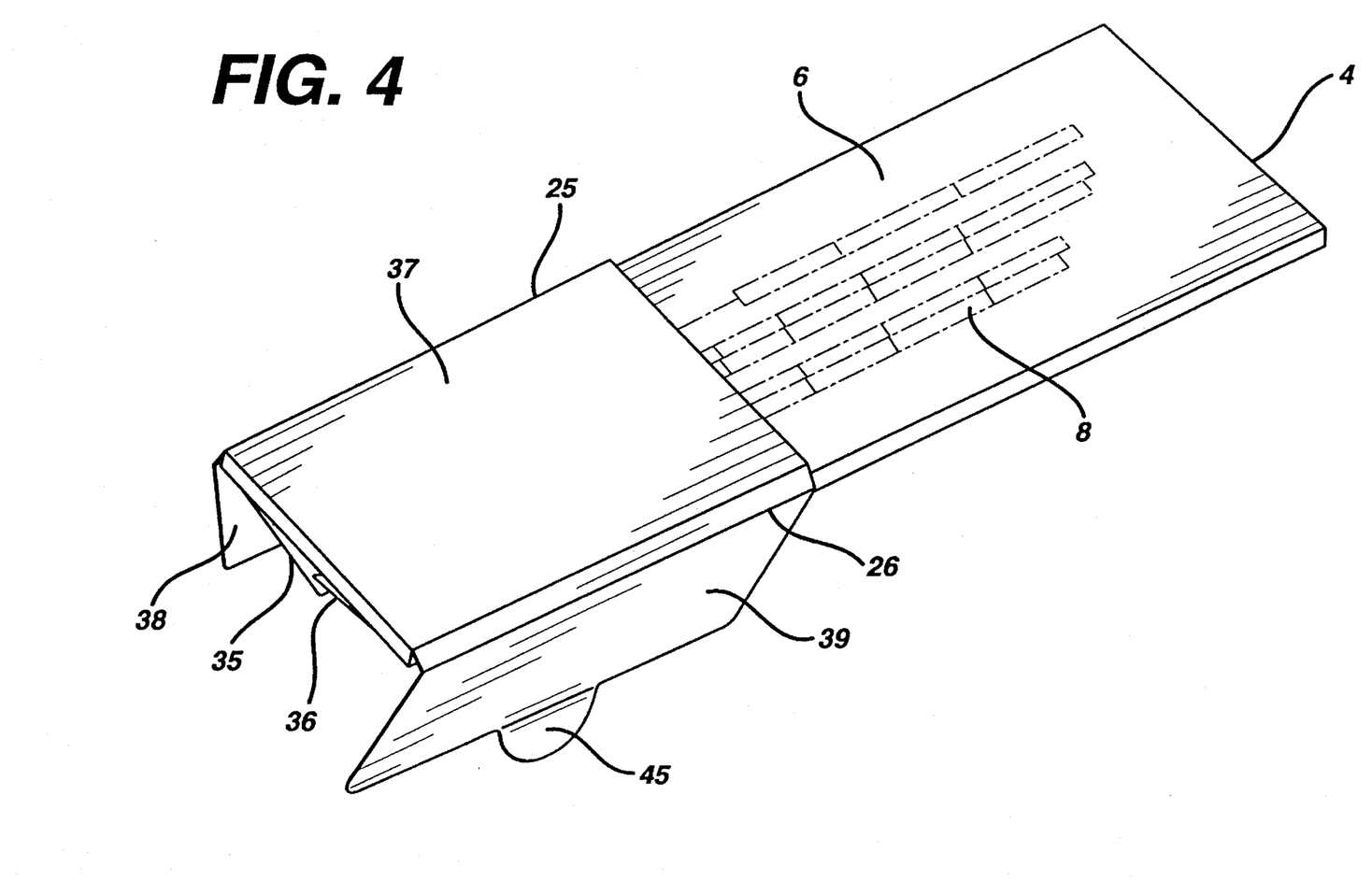

At the described kinking lines, which are formed by folds 30 or a series of holes 31, the needle-holding section 6 and the thread-holding sections 7 provided with the needle-thread combinations 20, 21 are folded like a concertina, as shown in FIGS. 2 to 4. The rear faces of the needle-holding section 6 and of the upper thread-holding section 7 are initially folded onto one another along the series of holes 31 so that they come into contact. Because of the series of holes 31 between the needle-holding section 6 and the thread-holding section 7, a fluted folding edge is formed in the shape of small semi-circles, by means of which the threads 21 bent around these folded edge are guided.

In addition, the front faces of the two thread-holding sections 7 are folded towards one another. Because of the thread holders 15 attached to the thread-holding sections 7, the two front faces of the thread-holding sections 7 are not able to come into contact and are therefore, as shown in detail in FIG. 5, arranged in spaced apart manner. The double fold 30 formed between the thread-holding sections 7 makes it possible for the two thread-holding sections 7 to run parallel to one another.

Next, as is shown in FIG. 3, the closure plates 35, 36 attached to the long edges of the needle-holding section 6 are bent back towards the rear face of the lower thread-holding section 7. Because of the double folds 27, 28, the spaced arrangement of the two thread-holding sections 7 is not disturbed. The tabs 43 of the closure plate 36 are now inserted into the incisions 44 of the closure plate 35 and bent over, by means of which it is ensured that the folded arrangement of the needle-holding section 6 and of the thread-holding sections 7 does not unfold.

Finally, as is shown in FIG. 4, the cover plate 37 is bent onto the front face of the needle-holding section 6. The cover plate 37 is preferably sized to cover the needles 20 and the front thread ends 22 secured to the front face of the needle-holding section 6. The closure plates 38, 39 of the cover plate 37 are now bent towards the closure plates 35, 36, and the tab 45 is inserted into the incision 46, the cover plate 37 thus being secured in its position. Here also, the double folds 25, 26 ensure that the spaced-apart arrangement of the two thread-holding sections 7 is not disturbed.

Figure 5:
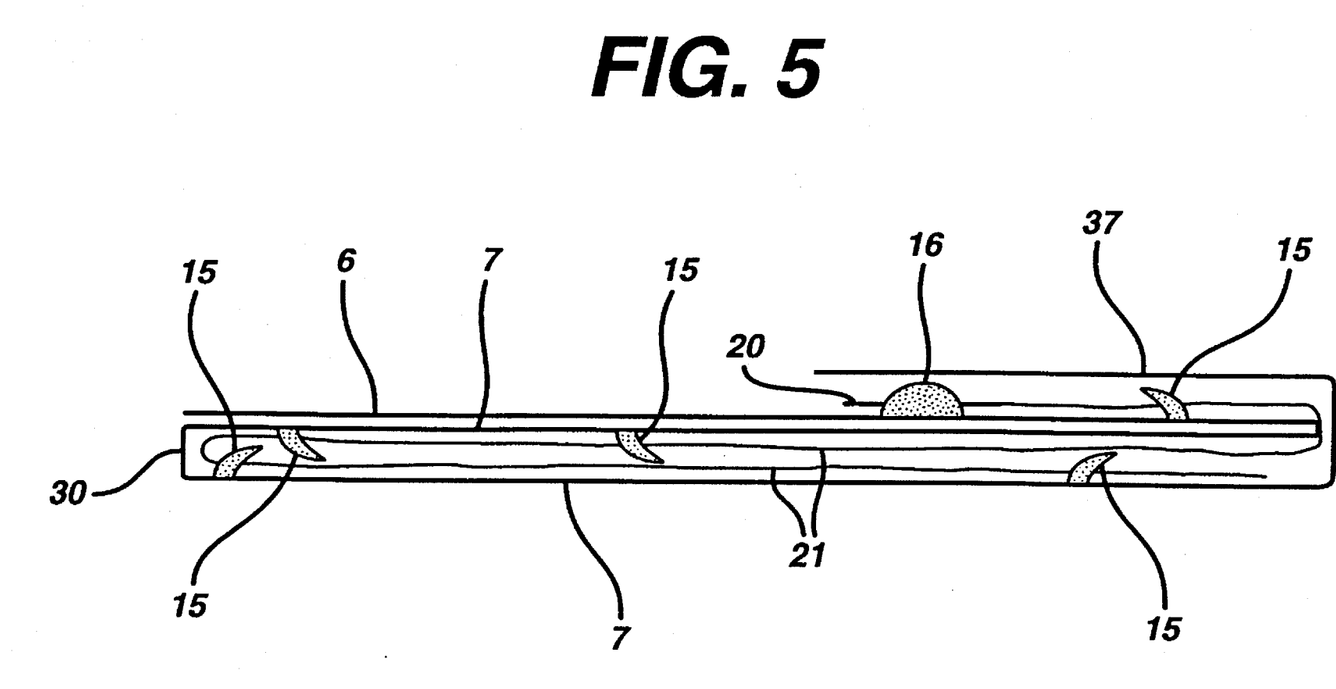

As is shown in FIG. 5, because of the concertina-shaped folding technique, the front faces of the thread-holding sections 7 lie in each case opposite one another in parallel and spaced-apart manner. The rear faces of the upper thread-holding section 7 and of the needle-holding section 6 also lie opposite one another and come into contact. AS described above, the needle holder 16 and the thread holders 15 are preferably arranged on the front face of the base plate 1. Since the thread holders 15 form a certain spatial elevation, the front faces of the two thread-holding sections 7 are kept spaced apart by the thread holders 15, whilst the rear faces of the upper thread-holding section 7 and of the needle-holding section 6 lie directly against one another. The closure plates 35, 36, 38, 39 are not indicated in FIG. 5.

The individual needle-thread combinations 20, 21 are attached to the front face of the needle-holding section 6 and of the thread-holding sections 7 and follow the fold pattern of these sections 6, 7. At those places where the front faces of the thread-holding sections 7 lie opposite one another in spaced-apart manner, the threads 21 consequently also lie directly opposite one another. At those places where the rear faces of the needle-holding section 6 and of the upper thread-holding section 7 lie opposite one another, the threads 21 secured on the associated front faces are held separate by precisely these sections 6, 7.

The thread holders 15 are manufactured as foam strips and have, as shown in FIG. 6a, holding slots 17, 19. The strips have, as shown in detail in FIG. 6b, a triangle-like cross-section, whereby the adhesive surface 11 runs flat and the adjacent surfaces 12, 13 are constructed in flat or curved manner. The interior angle, located between the adhesive surface 11 and the adjacent surface 13, of the triangle is greater than 90°, as a result of which an undercut is formed. The side edge 14 of the strip at which this undercut is formed, has, as shown in detail in FIG. 6a, a zigzag-shaped design. Consequently, the cross-sectional area of the strip changes, and the holding slots 19 which are placed on the tips of the zigzag pattern which project outwards, have a larger cross-sectional area than the holding slots 17 which are placed on the tips of the zigzag pattern which project inwards. Thick threads 21 are held in holding slots 19 with a large cross-sectional area and thin threads 21 are held in holding slots 17 with a small cross-sectional area.

The thread holders 15 are arranged such that the side edge 14 of the strip where this undercut is situated is placed in the direction in which the thread 21 moves when it is pulled out from the package (see FIG. 5). If the thread 21 held in the holding slots 17, 19 of the thread holders 15 is drawn in the pull direction upon removal, it moves, because of the shape of the cross-section described, upwards out of the holding slots 17, 19 of the individual consecutive thread holders 15 and can be removed from the package with reduced application of force, without high frictional forces or even a blockage being able to occur.

The shown package with surgical suture material is preferably placed in an outer package which is not shown. After sterilisation, for example by irradiation, the package shown remains sterile even when the outer package is then exposed to the non-sterile surroundings. During an operation, the outer package is torn open by operation personnel working in non-sterile conditions in such a way that they do not touch the package shown. Personnel operating in sterile conditions then pull the package out of the outer package, release the closure plates 38, 39 and open the cover plate 37 which can be completely folded back, whereby the surgeon now has direct access to the needles 20 and the threads 21 attached thereto. Written and colour markings 8 are provided on the visible surface of the needle-holding section 6, which allow the surgeon to pull a desired needle-thread combination 20, 21 out of the package.

The needle 20 is grasped by a gripping-device in the proximity of the front thread end 22 and pulled out of the needle holder 16. On removal, the thread 21 slides in the direction of pull through the holding slots 17, 19 of the thread holders 15. Consequently, the thread 21 moves, starting at the thread holders 15 placed at the double fold 30 (on the left-hand side in FIG. 5), out of the holder slots 17, 19 and can thus be removed safely from the described package.

We claim:

1. Package with surgical suture material a) having a base plate (1) which has a first long edge (2), a second long edge (3), an upper short edge (4) and a lower short edge (5), and an outer face, and which is divided by at least one fold (3) running transversely to the first and second long edges (2, 3) into a needle-holding section (6) starting at the upper short edge (4) and at least one thread-holding section (7) connected thereby, whereby provided at the needle-holding section (6) is at least one needle holder (16) and at each thread-holding section (7) at least one thread holder (15) running transversely to the first and second long edges (2, 3), b) having at least one needle-thread combination comprising a thread and a needle (20, 21) said needle (20) secured at a front thread end (22), whereby each needle-thread combination (20, 21) is disposed into the needle-holding section (6) and the thread-holding section (7), and whereby each thread (21) is held by a plurality of thread holders and the needles (20) are held by each needle holder (16), so that the threads (21) are kept spaced apart, or having one or several threads (21), whereby at least one thread (21) is disposed onto the needle-holding section (6) and at least one thread-holding section (7), and whereby each thread (21) is held by at least one thread holder (15) and the front end of each thread (22) is held by the needle holder (16), so that each thread (21) is kept spaced apart, c) whereby the base plate (1) is folded along folds (30) in concertina shape, so that each thread-holding section (7) and each needle-holding section (6) lie opposite one another, d) whereby, in the folded state of the base plate (1), the front end of each needle-thread combination (20, 21) and the needle holder (16) is located on the outer face of the folder base plate (1), e) and having first closure devices (35, 26) which are connected to the first and second long edges (2, 3) of the base plate (1), so that the folder base plate (1) is secured against unfolding, f) and having a cover plate (37) arranged such that it is able to be folded over at one of the upper or lower short edges (4, 5) in order to cover the front end of the needle-thread combinations (20, 21) or the front end of the threads (21) lying on the needle-holding section (6) and having second closure devices (38, 39) which are arranged at the cover plate (37) in order to hold the cover plate (37) bent into the needle-holding section (6) in this position, g) wherein the cover plate (37) is arranged at the lower short edge (5) of the base plate (1), and the second closure devices (38, 39) are arranged at the first and second long edges of the cover plate (37) and the first closure devices (35, 36) are arranged at the first and second long edges (2, 3) of the needle-holding section (6), h) wherein the first and second closure devices (35, 36, 38, 39) are designed as closure plates (35, 36, 38, 39) which can be folded around towards the folded base plate (1), and closure means (43, 45) are formed at the closure plates (36, 39) which engage with closure means (44, 46) of the corresponding closure plates (35, 38), i) wherein the cover plate (37) and the first and second closure plates (35, 36, 38, 39) are formed as one piece with the base plate (1), j) wherein the needle holder (16) is arranged at an angle to the first and second long edges (2, 3) of the base plate (1), k) wherein the location where the thread (21) is directed around section (6, 7) in the folded state of the base plate (1), each fold (30) is formed as a member of a series of holds (31), which represents an additional guide for each thread (21), l) wherein each thread holder (15) and each needle holder (16) is formed as glued-on foam strips which are provided with holding slots (17, 18, 19) which run transversely, m) wherein the form strips of the thread holders (15) have a triangular cross-section with a flat base face (11) and either a straight or curved face (12, 13), n) wherein an interior angle of the cross-section, formed by the flat base (11) and one face (13) is an obtuse angle, and o) wherein a side edge (14) of the foam strip is formed in zigzag shape, and each holding slot (17, 19) is arranged at different places of the strip, whereby different cross-sectional areas of each holding slots (17, 19) are thereby provided.

* * * * *